United States Patent [19]

Brovold

[11] 4,266,429
[45] May 12, 1981

[54] SELECTABLE DEPTH WATER RETRIEVER

[76] Inventor: Thomas E. Brovold, 7721 Chanhassen Rd. #142, Chanhassen, Minn. 55317

[21] Appl. No.: 76,197

[22] Filed: Sep. 17, 1979

[51] Int. Cl.³ ............................................. G01N 1/12
[52] U.S. Cl. ............................................. 73/425.4 R
[58] Field of Search ................................... 73/425.4 R

[56] References Cited

U.S. PATENT DOCUMENTS

| | | | |
|---|---|---|---|
| 2,155,442 | 4/1939 | Parkhurst | 73/425.4 R |
| 2,314,372 | 3/1943 | Spilhaus | 73/425.4 R |
| 4,004,463 | 1/1977 | Puthoff | 73/425.4 R |

FOREIGN PATENT DOCUMENTS 872821  7/1961  United Kingdom ............... 73/425.4 R

*Primary Examiner*—S. Clement Swisher
*Attorney, Agent, or Firm*—Wicks & Nemer

[57] ABSTRACT

A selectable depth water retriever including a weighted container having a threaded neck thereon which mounts a threaded cap. The cap has an opening formed in the top thereof. A perforated disc is positioned on the top of the neck of the container, and positioned between the perforated disc and a closure disc upon the cap opening is a coil spring which normally maintains the closure disc upon the cap opening until pressure at a selected water depth forces the closure disc from the cap opening to allow water to enter the container. The threaded connection of the cap upon the container allows for adjustment of the compression of the spring which in turn determines at what depth the closure disc is removed from the opening in the cap.

9 Claims, 4 Drawing Figures

U.S. Patent   May 12, 1981   4,266,429
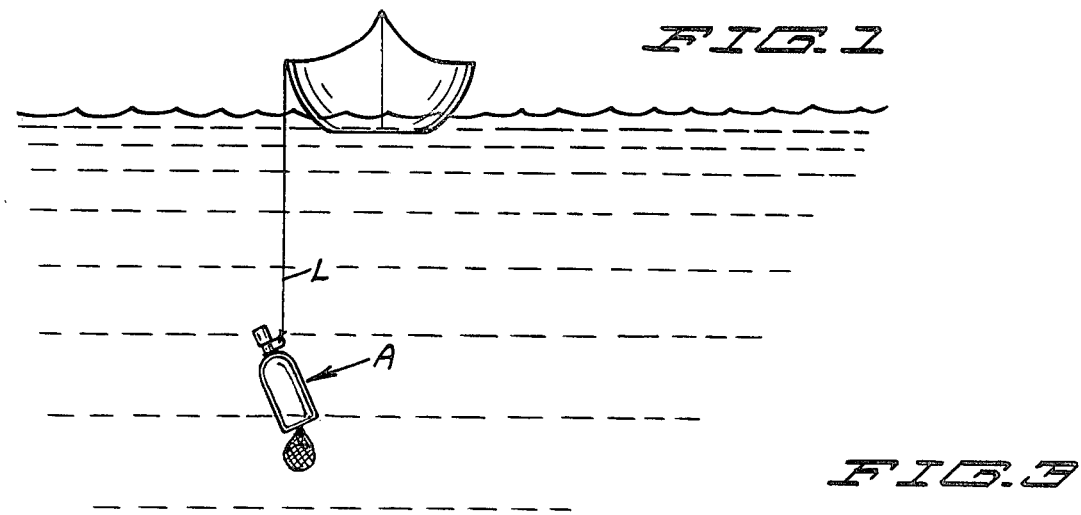
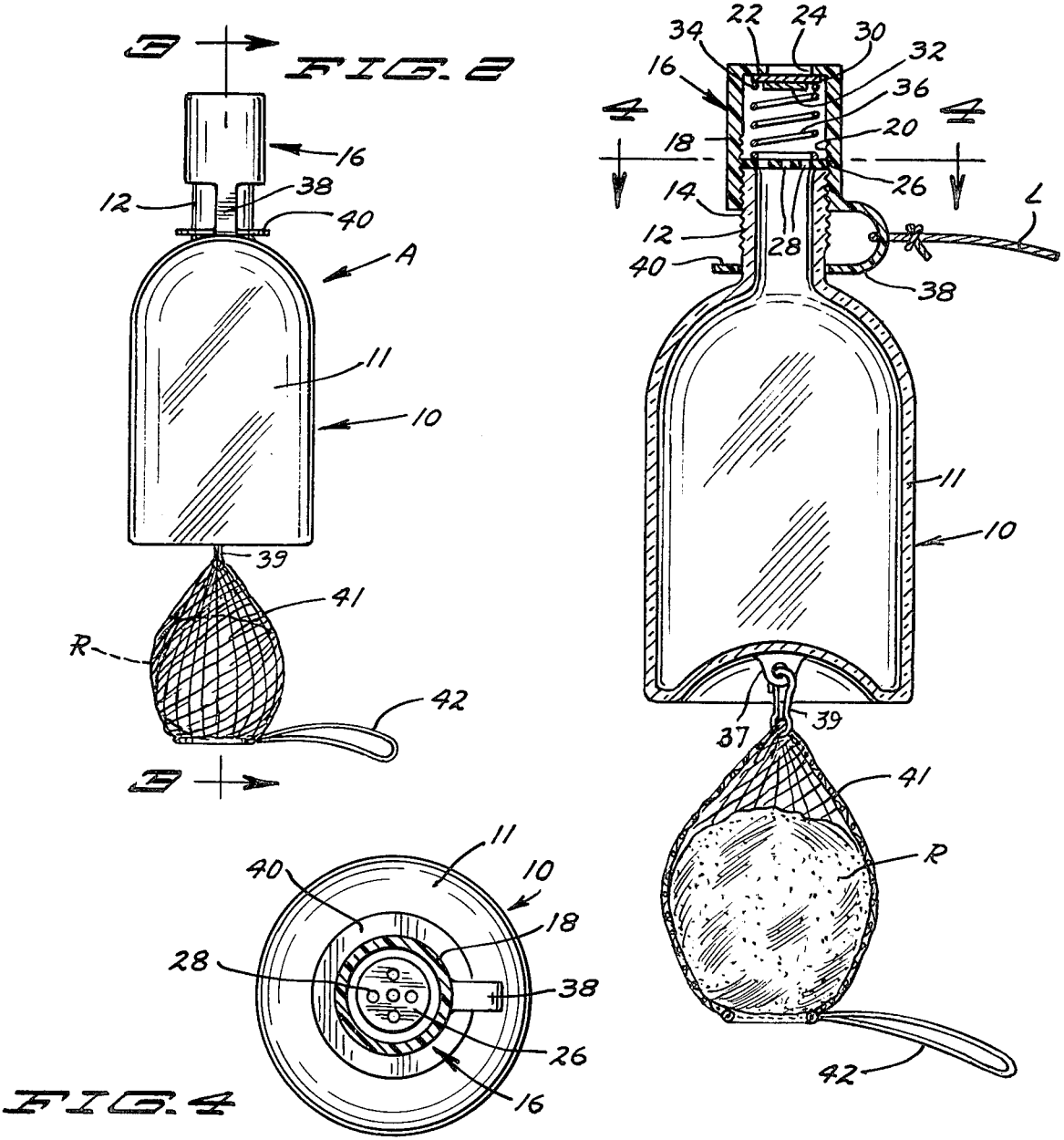

SELECTABLE DEPTH WATER RETRIEVER

SUMMARY

The invention relates to an improvement in a device for retrieving water from selected depths of a body of water such as a lake, river or the like.

In back packing, hunting, fishing and the like in remote uninhabited areas where fresh water is not available, it is desired to have a device for retrieving water from a lake or river, and the more desireable water generally from the standpoint of purity and cool temperature is found at some depth below the surface.

It is therefore an object of the invention to provide a weighted container for retrieving water at a selected depth below the surface. Such a container as disclosed herein has a retrieving line connected thereto and includes a cap threadedly mounted thereon, the cap having an opening formed in the upper end together with a spring interposed between a closure plug for the cap opening and a perforated disc positioned on an opening of the container.

The spring normally maintains the closure plug upon the cap opening at upper water levels whereby undesireable elements are prevented from entering the container, and as the weighted container is lowered in the water, the closure plug is forced from the cap opening due to water pressure at a depth which depends upon the degree of compression of the spring which is adjustable by means of the threaded cap upon the container or by use of a stronger spring. The closure plug returns to the cap opening due to less water pressure as the container is raised thereby sealing off the container against receiving anything but water at a selected depth. The device may also be used for water sampling.

In the drawings forming part of this application:

FIG. 1 is a side elevational view of a selectable depth water retriever embodying the invention and shown in a lowered position from a boat.

FIG. 2 is a further side elevational view of the retriever.

FIG. 3 is a sectional view on the line 3—3 of FIG. 2.

FIG. 4 is a sectional view on the line 4—4 of FIG. 3.

Referring to the drawings in detail the adjustable depth water retriever A includes the bottle 10 formed of the main hollow body portion 11. The bottle 10 may be formed of an inert plastic material. The upper end of the bottle body 11 terminates in the hollow neck 12 which is threaded externally as at 14. Further provided is the cap 16 having the annular wall 18 which is internally threaded as at 20 for threaded engagement with the threads 14 of the neck 12. The annular wall 18 terminates at its upper end in the top 22 which has formed therein the hole 24.

The numeral 26 designates a perforated disc of a diameter whereby it fits upon the upper end of the neck 12. The disc 26 has a series of holes 28 formed therethrough to allow entrance of water into the hollow body portion. Additionally provided is the plug disc 30 which has a diameter slightly greater than the diameter of the hole 24 of the cap whereby it can close off the hole 24 as hereinafter described. The plug disc 30 has a smaller disc 32 secured to the underside of the plug disc 30 concentrically thereof the outer edge of disc 32 which forms an annular shoulder 34.

The numeral 36 designates a coil spring interposed between the perforated disc 26 and the plug disc 30 with the disc 32 within a coil of the spring and the shoulder 34 maintaining the spring in alignment upon the longitudinal axis of the cap 16 and bottle neck 12. Normally the cap is screwed upon the neck sufficiently that the spring 36 urges the plug disc upon the hole 24 to close off the hole until a certain depth of water is reached at which point the water pressure forces the plug disc off the opening 24 at a rate prescribed by the spring. The spring is calibrated to make one revolution of the cap increase the number of feet beneath the water surface that the plug disc will remain closed by a predetermined amount. Thus the cap may be positioned so that water will not enter the bottle until it is submerged to a known selected depth.

The cap 16 has formed as part thereof the half loop 38 connected at one end to the lower edge of the cap with the other end of the half loop formed in a loop 40 and positioned about the neck 12. With the loop about the neck the cap may be screwed on or off the neck. The retriever line L is connected to the half loop 38 for use in lowering the device A into the water and raising the same. Formed on the bottom of the bottle 10 is the eye 37 engaged by the releasable hook 39 which is connected to the plastic mesh bag 41 with the draw string 42 at the lower end for closing off the bag. A weight such as a rock R is placed within the bag whereby the device is weighted and will sink in the water. With the cap screwed down until the coil spring is compressed to its solid length, the closure plug is maintained against the top 22 and hole 24 against displacement whereby water in the container cannot exit and with an empty bottle foreign elements cannot enter the bottle.

OPERATION

In using the device A for retrieving water in the depths of a body of water the same is lowered by means of the retriever line L the weight R causing the device to sink. As the bottle sinks to a certain level the water pressure causes the plug disc 30 to unseat from the hole 24 against the action of the spring 36 depending upon the setting of the cap upon the spring whereby water enters the hole 24 and passes through the holes 28 of disc 26 and into the bottle hollow body portion 10. As the bottle sinks, the plug disc 30 doesn't open until the water pressure is great enough which can be adjusted for depth to open by screwing the cap to or from the body 10 thereby changing the resistance of the spring or the resiliency of the spring may be changed to accomplish the same purpose. As a result of the above water may be retrieved at a selected depth. The bottle A is then raised and as it is raised the reduction in water pressure causes the plug disc to close upon the hole 24.

With the bottle 10 retrieved from the water the cap 12 may be removed and the water in the bottle removed therefrom as desired.

Having thus described the invention, what is claimed as new and desired to be secured by Letters Patent is:

1. A selectable depth water retriever comprising:
   (a) a container having
   (b) an opening,
   (c) a cover,
   (d) means mounting said cover on said container and over said opening,
   (e) said cover having an opening formed therein,
   (f) a sealing member associated with said cover opening,
   (g) a resilient member, (h) means positioning said resilient member between said sealing member and said opening of said container normally urging said sealing member upon said opening of said cover, (i) means for weighting said container, and (j) means for attaching a retrieving device to said container for lowering and raising the container in the water.

2. The device of claim 1 in which (a) said means mounting said cover includes threads formed on said cover engageable with threads formed on said container.

3. The device of claim 2 in which said cover includes (a) an annular wall having a top thereon in which said opening is formed.

4. The device of claim 1 in which said cover includes (a) an annular wall having a top formed thereon in which said opening is formed.

5. The device of claim 3 in which (a) said sealing member is a disc.

6. The device of claim 5 in which said means mounting said cover on said container is adjustable whereby the amount of water pressure required to open said sealing member against the action of said resilient when said container is submerged under water may be varied.

7. The device of claim 1 in which said means mounting said cover on said container is adjustable whereby the amount of water pressure required to open said sealing member against the action of said resilient when said container is submerged under water may be varied.

8. The device of claim 7 in which said resilient member is a coil spring.

9. The device of claim 5 in which said resilient member is a coil spring.

* * * * *